United States Patent [19]

Johnson

[11] Patent Number: 4,594,903
[45] Date of Patent: Jun. 17, 1986

[54] DIP TUBE SAMPLING MEANS FOR CHEMICAL REACTORS

[75] Inventor: Kirk B. Johnson, Howard, Pa.

[73] Assignee: Ethylene Corp, Murray Hill, N.J.

[21] Appl. No.: 672,921

[22] Filed: Nov. 19, 1984

[51] Int. Cl.$^4$ .............................................. G01N 1/14
[52] U.S. Cl. ............................... 73/863.83; 73/863.86;
73/863.81; 422/283
[58] Field of Search ........... 73/863.81, 863.82, 863.83,
73/863.84, 863.85, 863.86, 864.34, 864.35,
864.73, 864.74; 422/283

[56] References Cited

U.S. PATENT DOCUMENTS

| | | | |
|---|---|---|---|
| 2,318,463 | 5/1943 | Bussmann | 422/283 X |
| 2,534,181 | 12/1950 | Roberts | 73/863.86 X |
| 3,081,435 | 4/1963 | Miscoe et al. | 73/863.81 X |
| 3,561,274 | 2/1971 | Haurschild | 73/863.86 |
| 3,986,401 | 10/1976 | Peterson | 73/864.35 |
| 4,037,475 | 7/1977 | Topham | 73/863.83 X |
| 4,471,664 | 9/1984 | Mailliet et al. | 73/863.85 X |
| 4,489,779 | 12/1984 | Dickinson et al. | 73/864.34 X |

FOREIGN PATENT DOCUMENTS

| | | | |
|---|---|---|---|
| 1180300 | 2/1970 | United Kingdom | 73/864.73 |
| 2071846 | 9/1981 | United Kingdom | 73/863.86 |

Primary Examiner—Stewart J. Levy
Assistant Examiner—Tom Noland
Attorney, Agent, or Firm—Charles E. Temko

[57] ABSTRACT

A double tube sealed sampling device adapted to be incorporated into a dip tube for sampling the contents of a chemical reactor on a continuous or intermittent basis. In a preferred form, the device may be maintained in a sealed relationship to the reactor to avoid any contact with the contents of the reactor with the outside environment. In installed condition, the two tubes which are of relatively small diameter are shielded from turbulence within the reactor by the larger diameter hollow cylinder of the dip tube, thereby permitting the smaller diameter tubes to be formed from unreinforced polytetrafluorethylene (PTFE) or similar material.

4 Claims, 6 Drawing Figures

DIP TUBE SAMPLING MEANS FOR CHEMICAL REACTORS

BACKGROUND OF THE INVENTION

This invention relates generally to the field of chemical processing systems, and more particularly to and improved dip tube adapter permitting the removal of the contents of a reactor and/or introduction of additional materials into the reactor without the necessity of opening manways, or opening the bottom valve of the reactor vessel.

In the processing of corrosive and highly active chemicals on a commercial basis, reactions are carried out within the confines of a glass-lined reactor or similar vessel. These vessels are of varying capacity, and usually have a large upwardly facing opening referred to as a manway for the introduction of large quantities of materials, as well as a bottom valve for the removal of such materials after processing. Smaller openings are also provided for the addition during processing of additional reagents which are injected below the surface if the reacting material, the openings being provided with cylindrical tubes referred to as dip tubes, in the case of non-gaseous materials. When materials in gaseous form are injected, the tubes are closed at the distal end thereof, and holes in the sides of the tubes are provided for dispersing gases under pressure, such devices being referred to in the art as spargers.

During reacting of chemicals, it is often desirable, if not essential, to monitor reaction samples in terms of sample density, color phase separation, settling, etc. When the specimen is obtained through the bottom valve, a relatively large amount must be removed to obtain a representative sample. To open the manway is difficult, and causes wear and tear on the glass-lined parts and envelope gaskets. In addition, it exposes the operator to often dangerous and toxic chemicals.

SUMMARY OF THE INVENTION

Briefly stated, the invention contemplates the provision of an improved dip tube adapter including inlet and outlet tubes of relatively small diameter and a transversely extending flange which may be bolted to the corresponding flange of a dip tube in sealed relation. The two tubes extend inwardly to approximately 1 inch beyond the depth of the dip tube which when installed in a vessel nozzle shields the two tubes from turbulence. The outer ends of the tubes terminate at the lower surface of the flange, and communicate with steel or steel reinforced tubes which are welded to the upper surface of the flange. In a simpler form, one free end of the PTFE lined steel tubes is connected to a vacuum system which includes a vacuum pump, and a sight glass, ball check, assembly valves, and the necessary piping etc., to allow samples to be drawn by vacuum from and to the vessel. The other free end can be used to add liquids or gases to the vessel. By connecting the free ends in a piping loop, a second form is achieved wherein a pump in the loop draws fluid from the vessel up one tube and around the loop and back down the remaining tube into the vessel. This loop allows easy access to the reactive fluid and may contain any number of devices such as a sight glass for viewing fluid reactions, temperature, pH and conductivity monitoring devices, a sampling outlet and return, and an inlet for pumping fluids from drums and adding this fluid to the vessel. Shielded by the dip tube, the relatively small diameter tubes are projectible to the center of the reacting material, and are capable of removing, on a continuous or as needed basis, sufficient amounts of reacting material for sampling purposes as well as returning the same after examination thereof.

All of the above functions may be performed without opening the reactor manway, thus protecting the operator from chemical exposure, and saving wear and tear on expensive glass-lined parts.

BRIEF DESCRIPTION OF THE DRAWING

In the drawing to which reference will be made in the specification, similar reference characters have been employed to designate corresponding parts throughout the several views.

DETAILED DESCRIPTION OF THE DISCLOSED EMBODIMENTS

Figure 1:
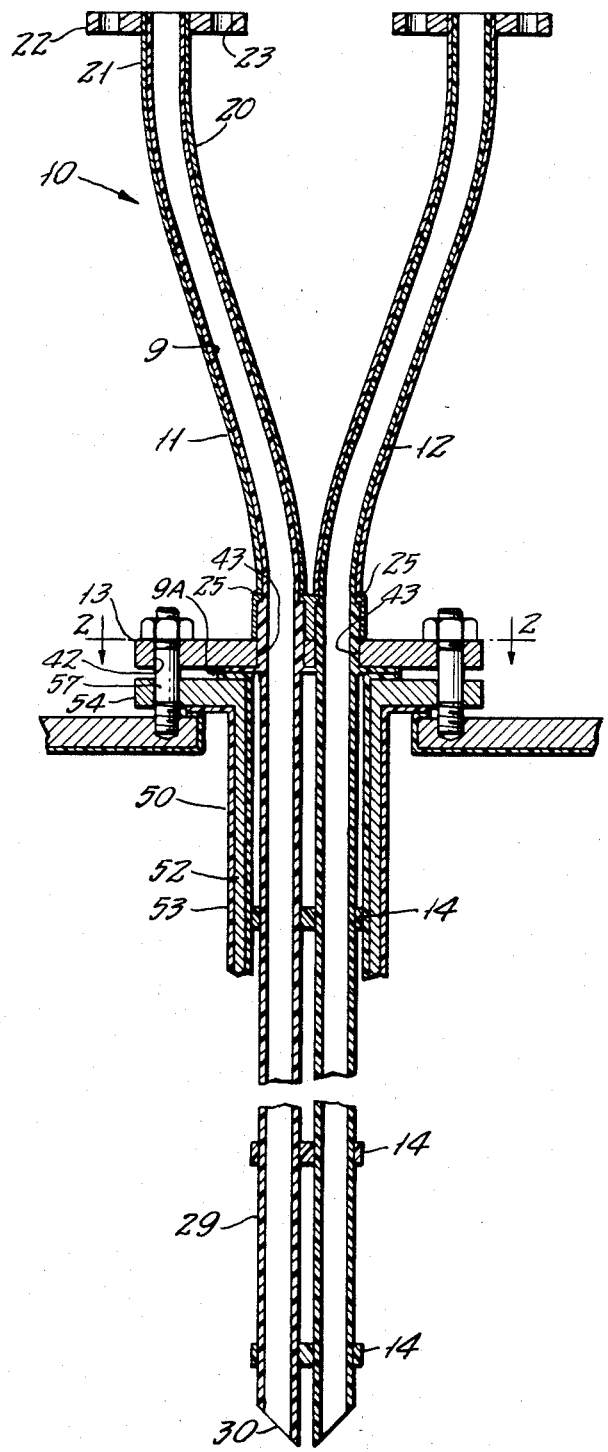
FIG. 1 is a schematic sectional view of an embodiment of the invention.
Figure 2:
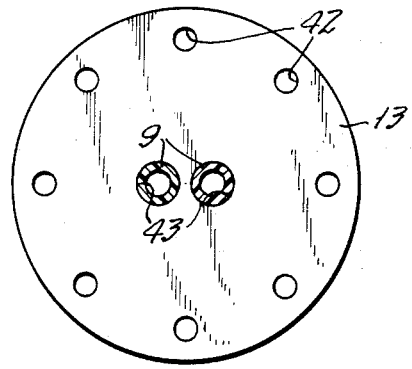
FIG. 2 is a transverse sectional view thereof as seen from the plane 2—2 in FIG. 1.
Figure 3:
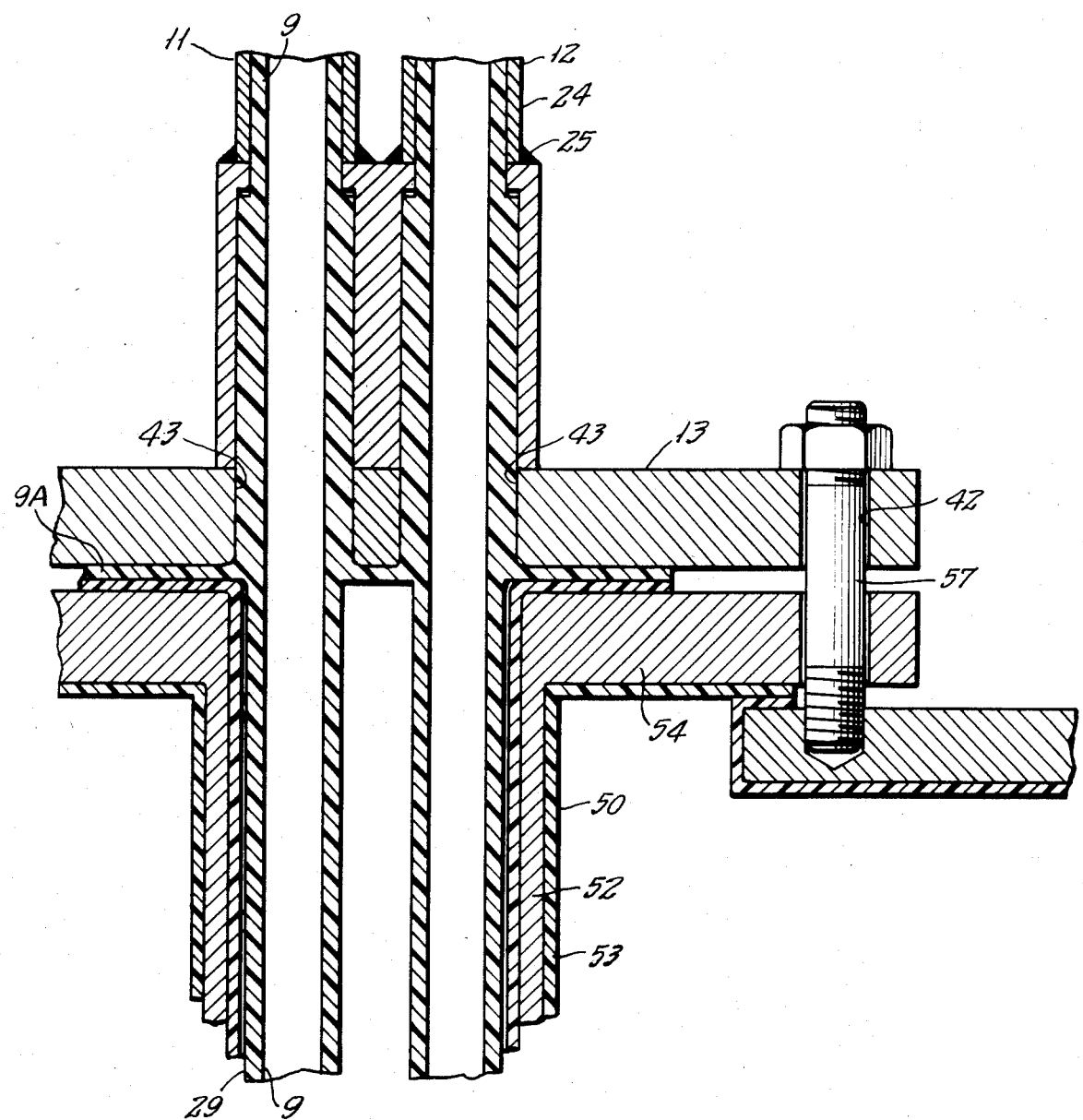
FIG. 3 is an enlarged fragmentary sectional view corresponding to the central portion of FIG. 1.

In accordance with the invention, the device, generally indicated by reference character 10, comprises broadly: first and second tube elements 11 and 12, respectively, a metallic composite flange element 13, and supporting spacers 14.

Each of the elements 11 and 12 include an upper tube member 20 having an upper free end 21 including a flange member 22 having openings 23 for bolted attachment to vacuum system piping, as required. A lower end 24 of member 20 terminates in welded areas 25 which secure the same to the flange element 13. The upper members 20 are preferrably formed from steel for suitable rigidity, and have a PTFE liner tube 9.

Each of the elements 11 and 12 include a lower member 29 which extends below the flange member 13 and terminates at the lower ends 30 in an angularly disposed edge. The PTFE liner tube 9 which is continuous from the top flange member 22 to the bottom lower end 30 of elements 11 and 12 has integral seal 9A and alignment spacers 14.

The flange element 13 reinforces the disc portion of integral seal 9A of PTFE and forces it against the flange 54 of the dip tube 50. The flange element 13 also includes peripheral bolt holes 42 for interconnection with the flange of the dip tube 50, and a first set of symmetrically disposed openings 43 through which the PTFE tube 9 passes.

The dip tube 50 includes a steel line cylindrical tube member 52 having a PTFE jacket 53 and mounting at one end thereof a transversely extending flange 54 which has its wetted surfaces PTFE covered. Through bolts 57 interconnect the flange element 13 with the flange 54 to thereby position the tube elements 11 and 12 within the tube 52. The former are maintained in spaced relation relative to the inside surface of the latter by PTFE alignment spacers 14 at periodic intervals.

Because the tube element 11 and 12 are shielded from turbulence while disposed within the tube 52, metallic reinforcing of the same is not necessary, and the internal diameters of the tube elements 11 and 12 may be correspondingly larger than would otherwise be the case. In most applications, but not necessarily all, one of the elements 11 and 12 becomes the suction leg and the other the return leg. The suction leg is preferably positioned into the direction of agitation for best operation.

Except where servicing is required, the device 10 may be permanenetly left interconnected to the dip tube.

Figure 4:
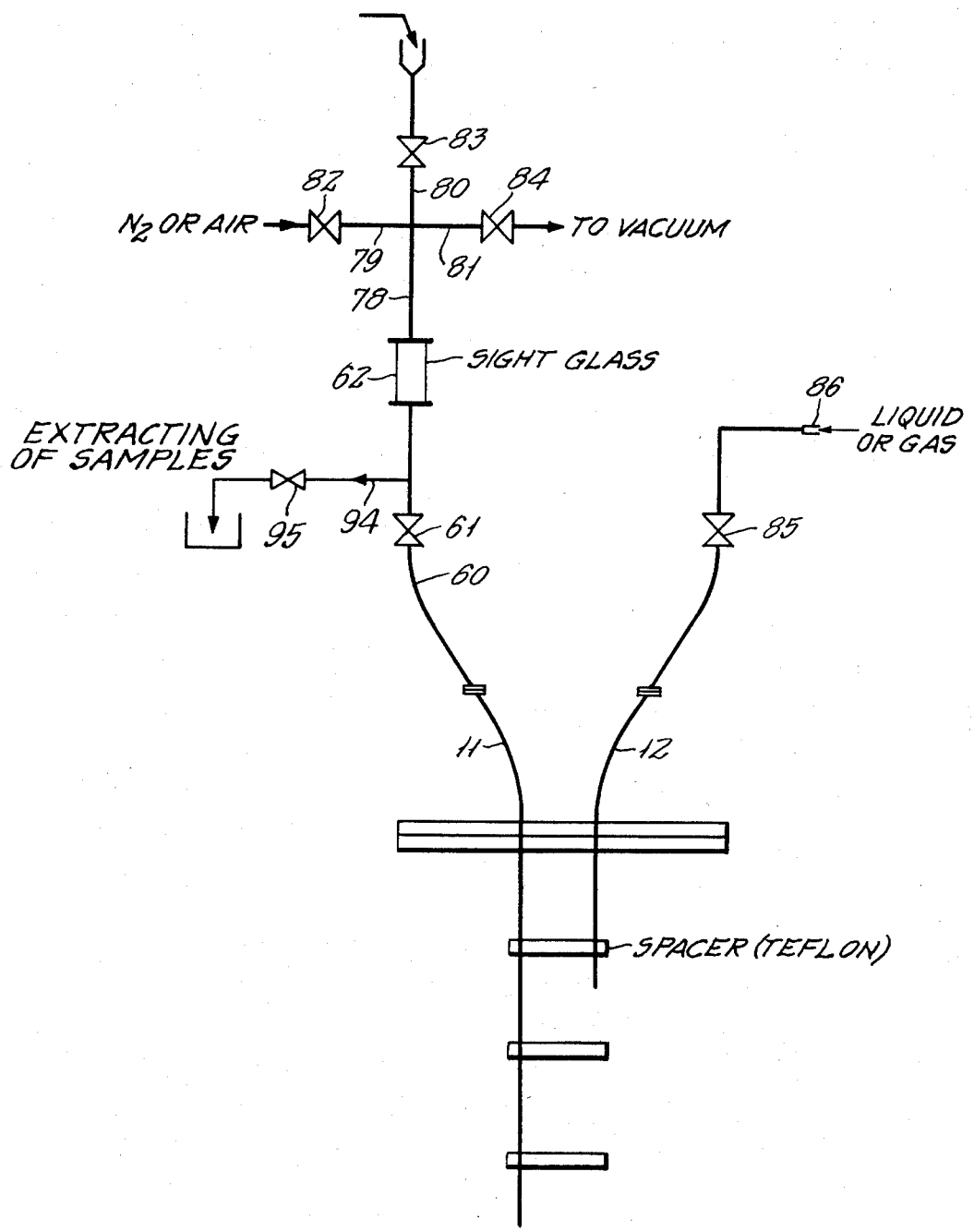
FIG. 4 is a schematic view showing one type of adapter external connection.

Turning now to FIG. 4 in the drawing there is illustrated one form of external circuitry connected to elements 11 and 12.

Figure 6:
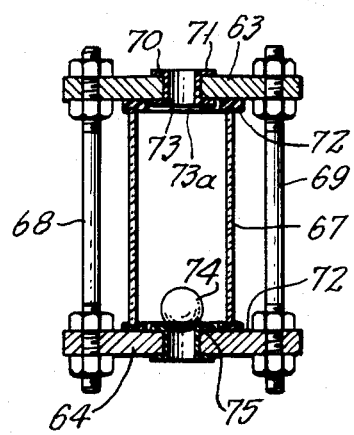
FIG. 6 is a schematic sectional view of a sight glass element in accordance with the invention.

Connected to element 11 is a length of tubing 60 leading to a stop cock 61 and thence to a tee and sight glass element 62, the details of which are illustrated in FIG. 6.

Referring to FIG. 6, the sight glass element 62 comprises upper and lower plates 63 and 64 to seal therebetween a glass tube 67. The plates are maintained in parallel relation by threaded members 68 and 69. The upper plate 63 has a PTFE liner 70 with the outer surface 71 for connecting two one inch lined fittings. The inner surface 72 is a machined seat for the glass tube 67. A seating surface 73a accommodates a hollow PTFE ball seat 74.

The lower plate 64 is similarly configured, but the corresponding seat 75 is fluted so as not to effect a sealing relation with the ball 74.

Referring to FIG. 4, above the sight glass element 62 is a conduit 78 leading to three conduits 79, 80 and 81 each fitted with a stop cock at 82, 83 and 84 respectively. Conduit 79 is used to introduce air or nitrogen. Conduit 80 communicates with a funnel for returning samples or the introduction of cleaning solvents or the like when necessary. Conduit 81 is connected to a vacuum source which permits the withdrawal of the contents of the reactor vessel to fill the sight glass for examination.

Element 12 is provided with a stop cock 85 communicating with a source of liquid or gas addition through a nozzle 86.

When it is desired to check the progress of a particular reaction batch, the vacuum source is actuated to permit the sight glass element 62 to be filled. When this is accomplished, the hollow teflon ball 74 floats to the upper end of the glass cylindrical 67, and seats in the valve seat 73 to prevent further flow. The valve 61 may then be closed to permit continuous observation of the contents of the sight glass element. A sample can be extracted at this point by closing valve 84 and opening valves 83 and 95. When completed, the vacuum is released, and the valve 61 opened to permit the contents of the sight glass to return to the reactor.

Figure 5:
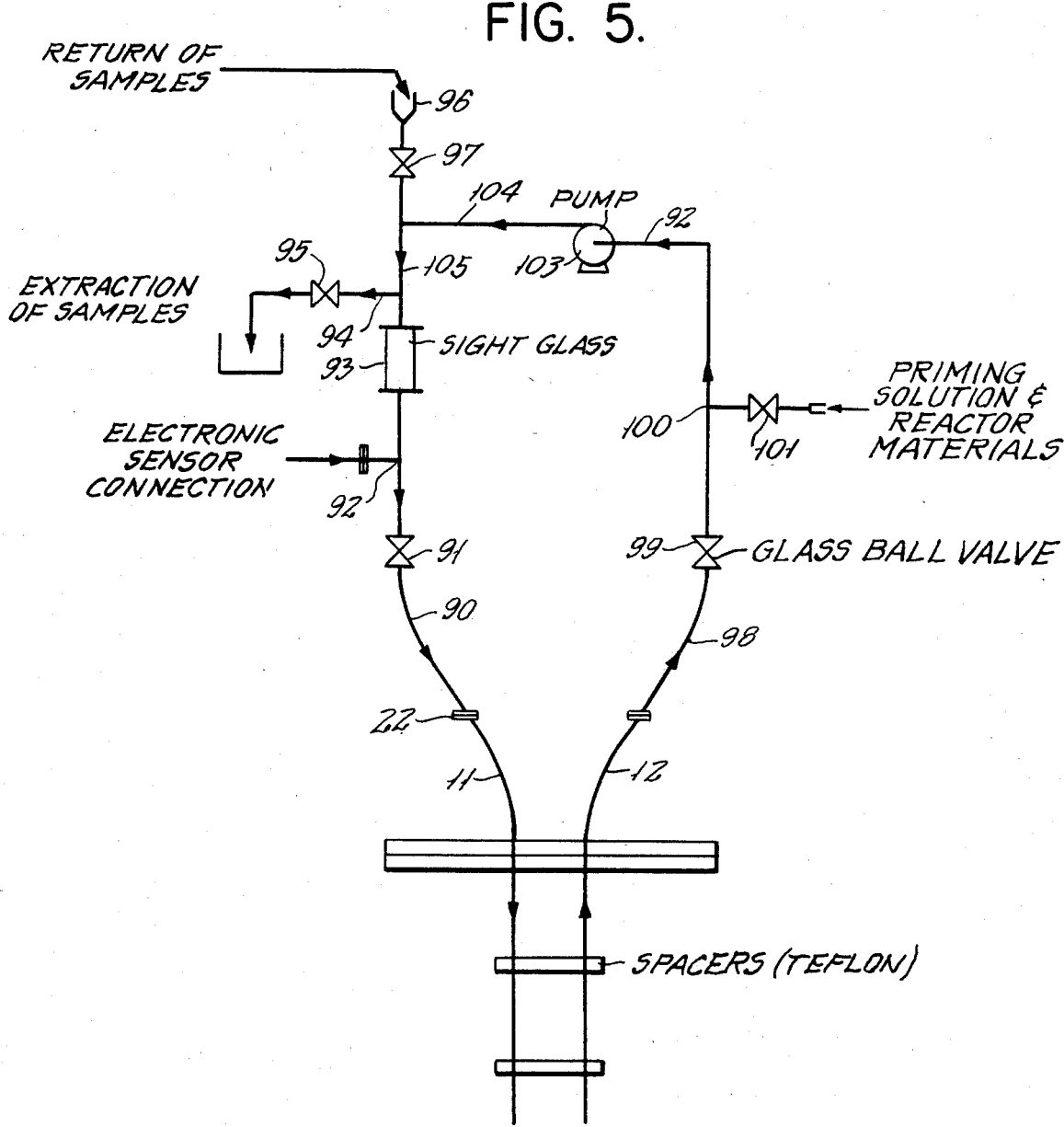
FIG. 5 is a schematic view showing a second type of adapter external connection.

Referring to FIG. 5, there is illustrated a second type of external circuit for use with the device 10, of somewhat more sophisticated nature.

Here, element 11 connects through a conduit 90 and valve 91 to a first connection 92 having a flange for the attachment of known electronic sensors for determining temperature, pH, and conductivity of the reacting mass. The sight glass corresponds to that shown in FIG. 4, but does not include the valve structure. A sample port 94 including a valve 95 is provided to permit samples to be withdrawn for laboratory analysis, which can be returned to the batch through funnel 96 and valve 97. It should be noted that with the use of glass ball valves, the use of the sight glass element 62 may be eliminated.

The element 12 connects with conduit 98 and glass ball valve 99 to a connection 100 and valve 101 for the introduction of reactor materials, cleaning solvents, or the like. The conduit 92 connects to a diaphragm pump 103 in turn connecting to conduit 104 and conduit 105 to provide a continuous loop whereby reacting material can be withdrawn through element 12 and returned through element 11. The pump 103 may be operated continuously or intermittently, and as required, and is preferably of a type compatible with the reacting materials.

It will be apparent that once the reactor vessel has been charged, the manway may be closed, and subsequent operation prior to completion of processing be performed using only the device 10 for access to the interior of the reactor vessel. The service personnel are thus effectively shielded from exposure to the reacting mass while introduction of smaller amounts of material, and sampling of the reacting mass is possible on either a continuous or intermittent basis as required.

I wish it to be understood that I do not consider the invention limited to the precise details of structure shown and set forth in this specification, for obvious modifications will occur to those skilled in the art to which the invention pertains.

I claim:

1. An improved dip tube adapter for use in sampling reacting material in a vessel comprising: first and second tube elements and a flange element supporting said tube elements at a medial point thereon; said tube elements being disposed in mutually parallel relation and passing through said flange element; that part of said first and second tube elements on one side of said flange element being formed of steel reinforced PTFE tubing; that part of said first and second tube elements on the opposite side of said flange element being formed of unreinforced PTFE tubing; said flange element having means for engaging a corresponding flange on a dip tube, whereby said second mentioned parts of said first and second tubes are positioned within said dip tube to be protected thereby.

2. An adapter in accordance with claim 1, further characterized in said flange element being of composite form including metal and PTFE laminae said metal reinforced parts being welded to said metal lamina, and said unreinforced parts being integrally formed with said PTFE lamina.

3. In combination, a dip tube including a hollow cylindrical tube member of given internal diameter and a transversely extending mounting flange surrounding said dip tube member; a dip tube adapter comprising a pair of parallel tube elements, each of external diameter less than said given internal diameter, and a transversely extending flange element surrounding said pair of tube elements at medially disposed portions thereof; said adapter being positioned within said dip tube such that said pair of tube elements is disposed within said hollow cylindrical tube to be thereby shielded, said flange of said adapter being juxtaposed and secured to said flange of said dip tube; a conduit connected to one of said tube elements, a sight glass connected in series with said conduit, and a vacuum source connected in series with said sight glass, said sight glass including a one-way check valve preventing fluid flow outwardly of said sight glass in a direction toward said vacuum source.

4. The combination in accordance with claim 3, further comprising: a second conduit connected to the other of said tube elements, a ball valve in series with said second conduit, and a fluid pump interconnected to the first and second conduits to form a loop element between the first and second tube elements.

* * * * *